United States Patent [19]
Abrahami

[11] Patent Number: 5,833,693
[45] Date of Patent: Nov. 10, 1998

[54] DRILL GUIDE

[76] Inventor: Israel Abrahami, 38 HaAlon Street, Timrat 23840, Israel

[21] Appl. No.: 850,185

[22] Filed: May 2, 1997

[51] Int. Cl.6 .................................................. A61B 17/56
[52] U.S. Cl. ............................................. 606/96; 433/172
[58] Field of Search ................................ 606/96, 97, 98, 606/80, 79, 86; 433/165, 167, 172, 173, 174

[56] References Cited

U.S. PATENT DOCUMENTS

| | | | |
|---|---|---|---|
| 4,299,212 | 11/1981 | Goudfrooy | 606/96 |
| 4,325,373 | 4/1982 | Silvenko et al. | |
| 4,360,012 | 11/1982 | McHarrie et al. | 606/96 |
| 4,865,025 | 9/1989 | Buzzi et al. | 606/96 |
| 4,920,958 | 5/1990 | Walt et al. | 606/96 |
| 5,234,434 | 8/1993 | Goble et al. | 606/96 |
| 5,350,383 | 9/1994 | Schmieding et al. | 606/96 |
| 5,562,664 | 10/1996 | Durlacher et al. | 606/96 |
| 5,613,971 | 3/1997 | Lower et al. | 606/96 |
| 5,620,449 | 4/1997 | Faccioli et al. | 606/98 |
| 5,643,273 | 7/1997 | Clark | 606/96 |

*Primary Examiner*—Guy V. Tucker
*Attorney, Agent, or Firm*—Helfgott & Karas, P C.

[57] ABSTRACT

A drill guide including a location pin, a guide block mechanically linked to the location pin and formed with a through hole for guiding therethrough a drill bit, the guide block being movable relative to the location pin in at least one of six degrees of freedom, and a fastener engageable with the guide block for fixing the guide block relative to the location pin.

12 Claims, 4 Drawing Sheets

DRILL GUIDE

FIELD OF THE INVENTION

The present invention relates generally to drill guides, and particularly to dental drill guides.

BACKGROUND OF THE INVENTION

Treatment of edentulous patients with osseointegrated fixtures made of titanium is a well known procedure in the dental art. The procedure includes installing a fixture in the alveolar bone of an at least partially edentulous jaw. Usually about four months are required for proper healing after fixture installation in the mandible, while about six months are required after installation in the maxilla. After healing, an abutment is installed on the upper portion of the fixture. After about two weeks, an artificial tooth may be screwed on to the abutment and the procedure is completed.

Installing the fixture requires drilling a series of holes in the alveolar bone. These holes must be properly aligned with each other in order to correctly install a row of fixtures. Unfortunately, in accordance with current methods and apparatus, alignment of holes is difficult and tedious.

U.S. Pat. No. 4,325,373 to Slivenko et al. describes a drill guide for forming an osteotomy for a dental implant. The drill guide includes a locating pins and a slide block that carries a pair of annular drill guide bushings which define drill bores, the axes of which are parallel and lie in a plane containing the axes of the locating pins. The drill guide bushings may be located along the slide block to a position for guiding a drill bit therethrough.

SUMMARY OF THE INVENTION

The present invention seeks to provide a novel and improved dental drill guide particularly useful for correct drilling holes for installment of implant fixtures, as well as other dental procedures which require accurate alignment of a series of holes. The drill guide of the present invention allows drilling holes in the mandible or maxilla, the holes being accurately spaced one from each other and correctly positioned in relation to adjacent teeth. The drill guide accurately guides the drill bit to drill a hole at the required angle in relation to the inclination of the alveolar bone. The holes are drilled parallel to each other for their entire depth. The drill guide is provided with interchangeable parts to allow drilling holes of incrementally larger diameters.

It is appreciated that the drill guide is not limited to dental use and may be used for drilling any kind of holes.

There is thus provided in accordance with a preferred embodiment of the present invention, a drill guide including a location pin, a guide block mechanically linked to the location pin and formed with a through hole for guiding therethrough a drill bit, the guide block being movable relative to the location pin in at least one of six degrees of freedom, and a fastener engageable with the guide block for fixing the guide block relative to the location pin.

In accordance with a preferred embodiment of the present invention, the drill guide includes a reference block from which protrudes the location pin, wherein the guide block is attached to the reference block and is movable relative to the reference block in at least one of six degrees of freedom.

Additionally in accordance with a preferred embodiment of the present invention, the guide block is movable relative to the location pin generally along a linear axis and may be rotated generally about the linear axis.

Further in accordance with a preferred embodiment of the present invention, the fastener fastens the guide block to the reference block.

Still further in accordance with a preferred embodiment of the present invention, the guide block includes an extension arm which slidingly mates with an aperture formed in the reference block.

In accordance with a preferred embodiment of the present invention, the location pin and/or extension arm includes calibrated markings along an axial length thereof Additionally in accordance with a preferred embodiment of the present invention, the reference block may be rotated relative to the location pin generally about a longitudinal axis of the location pin.

Further in accordance with a preferred embodiment of the present invention, the location pin is removably attached to the reference block.

Still further in accordance with a preferred embodiment of the present invention, the extension arm includes a flexible portion which may be bent relative to the reference block.

In accordance with a preferred embodiment of the present invention, the location pin is interchangeable for another the location pin having a different diameter. In addition, the guide block may be interchangeable for another the guide block having a different diameter through hole.

Further in accordance with a preferred embodiment of the present invention, the guide block and/or the reference block includes a handle.

Still further in accordance with a preferred embodiment of the present invention, the drill guide may include one or more ancillary blocks each mechanically linked to one another and formed with a through hole for guiding therethrough a drill bit, each ancillary block being movable relative to another ancillary block in at least one of six degrees of freedom, wherein one of the ancillary blocks is mechanically linked to the at least one guide block and is movable relative to the at least one guide block in at least one of six degrees of freedom, and a fastener engageable with each ancillary block for fixing the ancillary block relative to at least one of another ancillary block and the at least one guide block

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
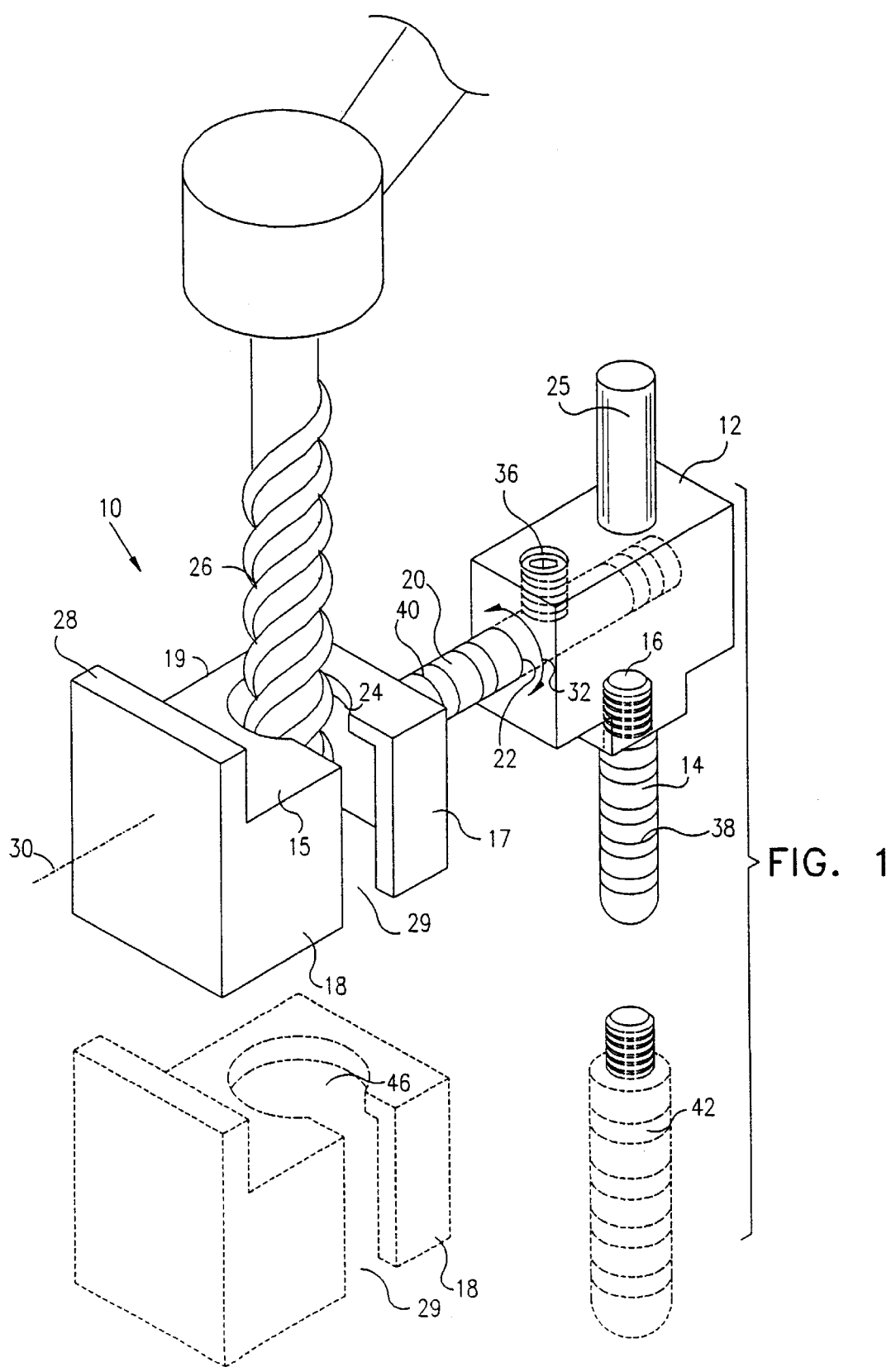
FIG. 1 is a simplified pictorial illustration of a drill guide, constructed and operative in accordance with a preferred embodiment of the present invention.
Figure 2:
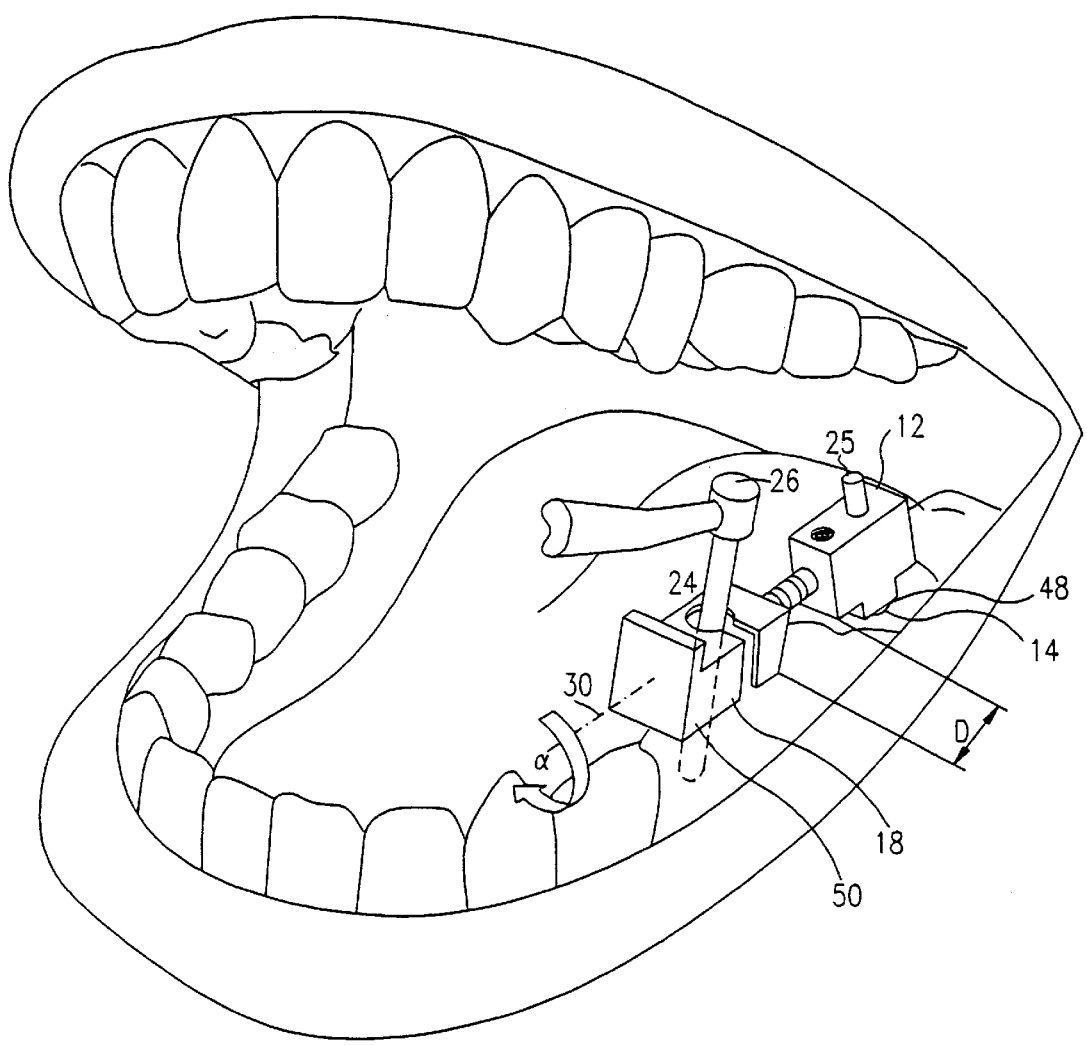
FIG. 2 is a simplified pictorial illustration of the drill guide of FIG. 1 being used to guide drilling of holes in a mandible, in accordance with a preferred embodiment of the present invention.

Reference is now made to FIGS. 1 and 2 which illustrate a drill guide 10, constructed and operative in accordance with a preferred embodiment of the present invention.

Drill guide 10 preferably includes a reference block 12 from which protrudes a location pin 14. Location pin 14 is preferably removably attached to reference block 12, such as by means of threaded attachment thereto, as shown at reference numeral 16.

Drill guide 10 further includes a guide block 18 which preferably includes an extension arm 20 which slidingly mates with an aperture 22 formed in reference block 12. Extension arm 20 and aperture 22 are preferably, although not necessarily, generally perpendicular to location pin 14. Reference block 12, location pin 14, guide block 18 and extension arm 20 are preferably constructed of durable materials suitable for dental surgery, such as stainless steel. Guide block 18 is formed with a through hole 24 for guiding therethrough a drill bit 26. Guide block 18 preferably, although not necessarily, includes a handle 28. Similarly, reference block 12 preferably, although not necessarily, includes a handle 25 (illustrated in FIGS. 1 and 2). Handle 25 preferably, although not necessarily, is generally axially aligned with location pin 14.

One or more view apertures 29 are preferably formed in guide block 18, so as to permit a user to see drill bit 26 pass through guide block 18. View apertures 29 may be formed, for example, on opposite faces 17 and 19 of guide block 18. As seen in FIG. 1, view aperture 29 may be formed on face 17 as well as a top face 15, thereby forming a continuous opening with hole 24 and thus providing a fill view of drill bit 26. Optionally, as shown hereinbelow in FIGS. 3 and 4, view aperture 29 may be formed only on face 17.

Guide block 18 is linearly movable relative to reference block 12 and location pin 14 generally along a linear axis 30, generally along extension arm 20, and may be rotated generally about axis 30, as indicated by an arrow 32. Preferably a fastener 36 is provided that is engageable with guide block 18 for fixing guide block 18 relative to location pin 14. For example, as illustrated in FIG. 1, fastener 36 may be a set screw which may be tightened against extension arm 20 to hold guide block 18 fixed relative to reference block 12.

Preferably location pin 14 and extension arm 20 include calibrated markings 38 and 40, respectively, along an axial length thereof Calibrated markings 38 and 40 help indicate a position or orientation of location pin 14 or guide block 18 with respect to a hole or bone, for example.

Drill guide 10 is preferably provided with interchangeable parts to allow drilling holes of incrementally larger diameters. For example, there may be provided a plurality of location pins with different diameters, such as a location pin 42 with a larger diameter than location pin 14. Similarly, there may be provided a plurality of guide blocks with different diameter holes, such as a guide block 44 with a hole 46 larger than hole 24.

Reference is now made to FIG. 2 which illustrates drill guide 10 being used to guide drilling of holes in a mandible of a patient, in accordance with a preferred embodiment of the present invention. Location pin 14 is inserted in a hole 48 previously drilled in the mandible. Guide block 18 is oriented at a distance D from reference block 12 and rotated an angle α about axis 30, distance D and angle α being determined by the particular geometry of the patient's mouth. Fastener 36 is then tightened to secure guide block 18 relative to reference block 12.

After drilling a hole 50 with drill bit 26 guided through hole 24 of guide block 18, drill guide 10 may be removed from holes 48 and 50. Location pin 14 may then be placed in freshly drilled hole 50 for aligning drilling of the next hole. The procedure may be repeated for as many holes as required, and different location pins and/or guide blocks may be used to incrementally drill larger size holes.

Figure 3:
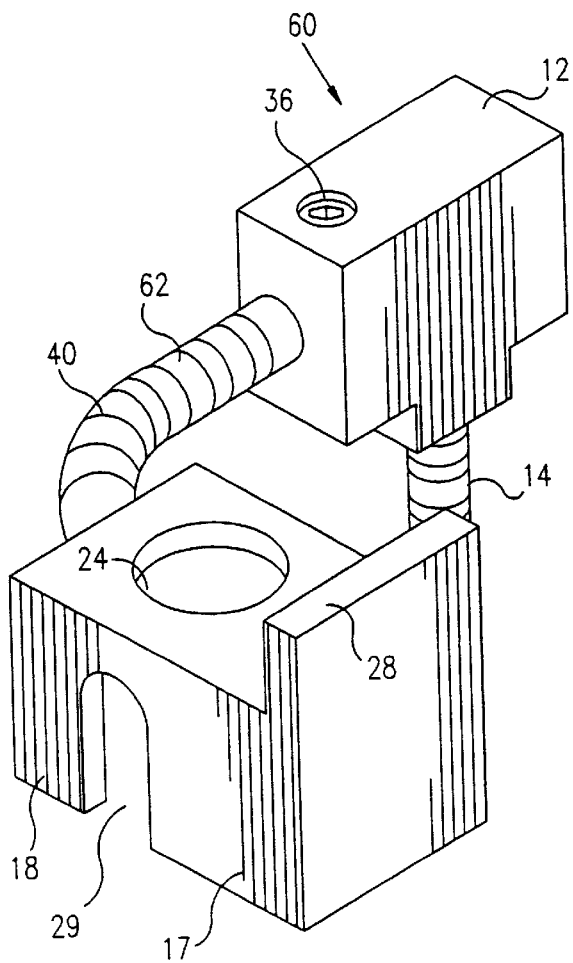
FIG. 3 is a simplified pictorial illustration of a drill guide, constructed and operative in accordance with another preferred embodiment of the present invention, and including a flexible extension arm protruding from a guide block.

Reference is now made to FIG. 3 which illustrates a drill guide 60, constructed and operative in accordance with another preferred embodiment of the present invention. Drill guide 60 is preferably substantially identical to drill guide 10, with like elements being referenced by like numerals. Drill guide 60 differs from drill guide 10 by including a flexible extension arm 62 that protrudes from guide block 18. Flexible extension arm 62 may be bent in a variety of manners so as to bring guide block 18 into a desired orientation relative to reference block 12, arm 62 preferably having sufficient rigidity to maintain the bent shape so as to permit steady, accurate drilling of holes through hole 24. Flexible extension arm 62 allows moving guide block 18 relative to location pin 14 in any of six degrees of freedom.

Figure 4:
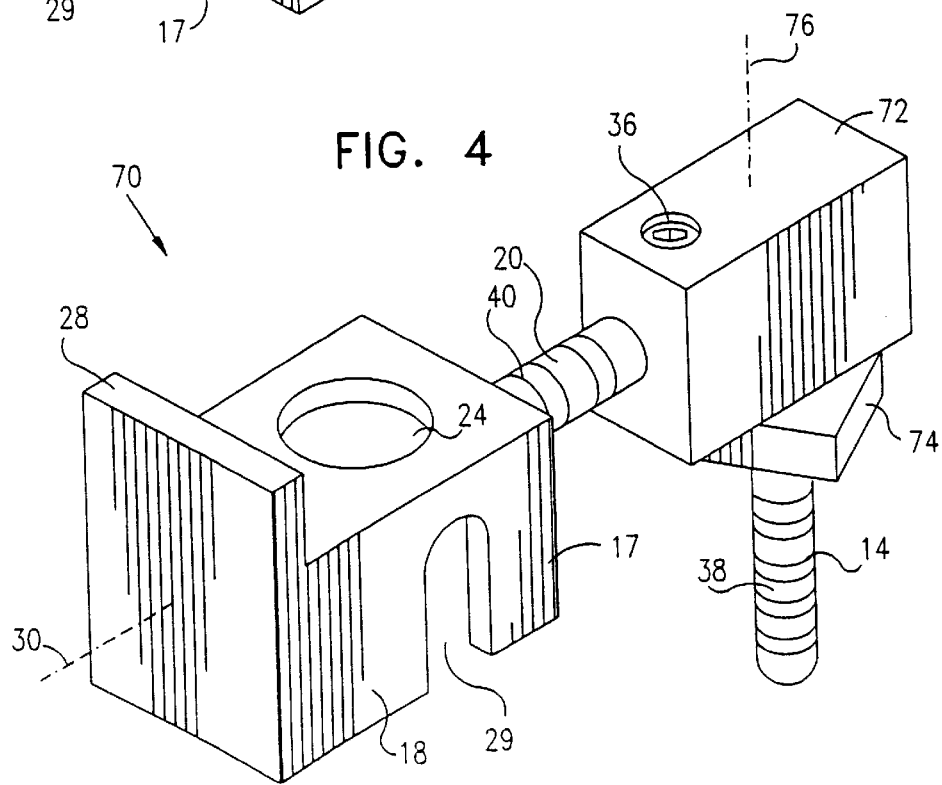
FIG. 4 is a simplified pictorial illustration of a drill guide, constructed and operative in accordance with yet another preferred embodiment of the present invention, and including a reference block which rotates relative to a location pin.

Reference is now made to FIG. 4 which illustrates a drill guide 70, constructed and operative in accordance with yet another preferred embodiment of the present invention. Drill guide 70 is preferably substantially identical to drill guide 10, with like elements being referenced by like numerals. Drill guide 70 differs from drill guide 10 by including a reference block 72 which rotates relative to location pin 14. Reference block 72 may, for example, be rotatably mounted on a base 74 to which is attached location pin 14, so that reference block 72 may be rotated generally about a longitudinal axis 76 of location pin 14.

Figure 5:
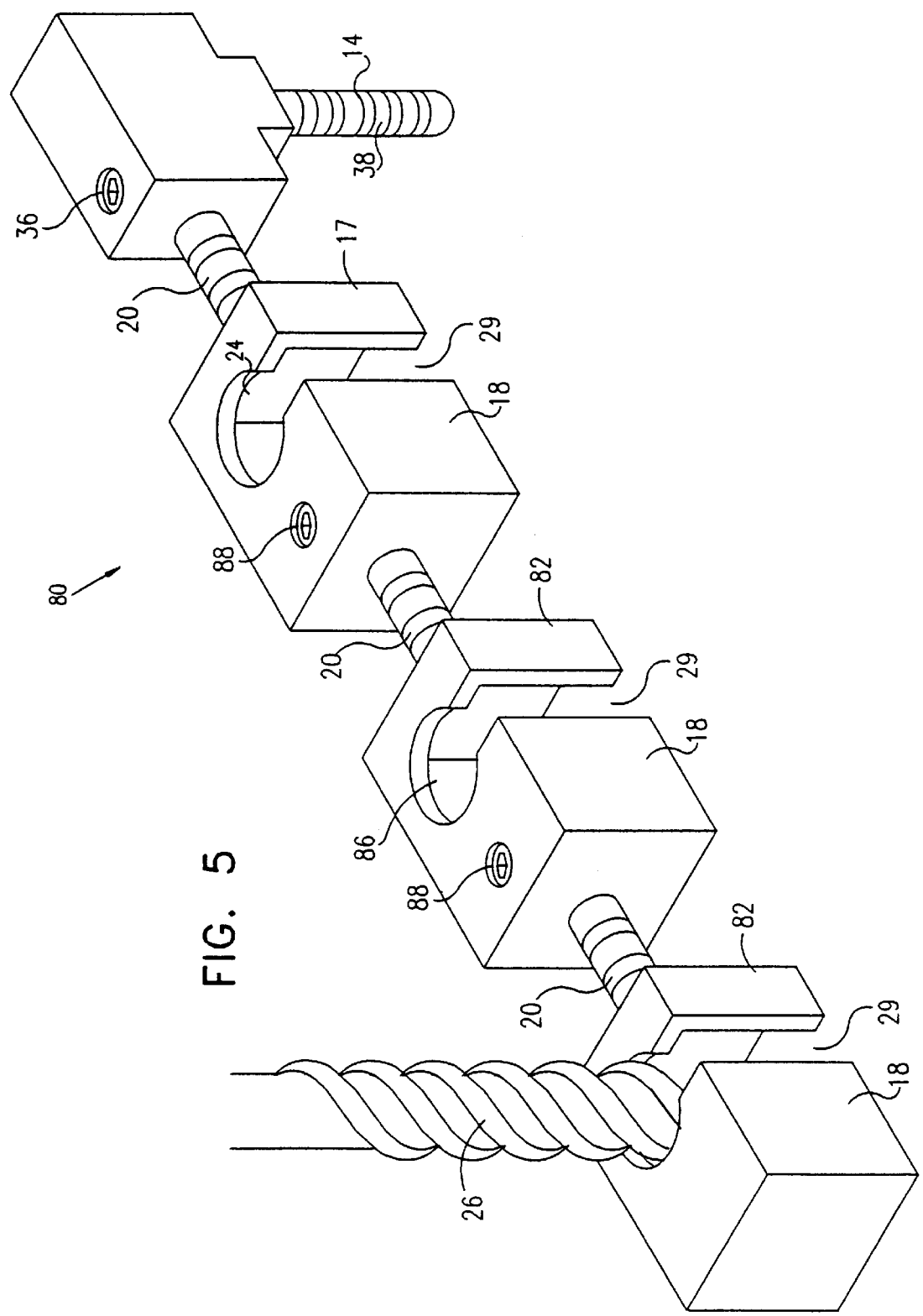
FIG. 5 is a simplified pictorial illustration of a drill guide, constructed and operative in accordance with still another preferred embodiment of the present invention, and including a plurality of ancillary blocks mechanically linked to one another.

Reference is now made to FIG. 5 which illustrates a drill guide 80, constructed and operative in accordance with still another preferred embodiment of the present invention. Drill guide 80 is preferably substantially identical to drill guide 10, with like elements being referenced by like numerals. Drill guide 80 differs from drill guide 10 by including one or more ancillary blocks, two being illustrated in FIG. 5 and referenced by numerals 82 and 84, and each mechanically linked to one another and formed with a through hole 86 for guiding therethrough a drill bit, such as drill bit 26. Ancillary blocks 82 and 84 are preferably movable relative to each other in at least one of six degrees of freedom, such as by means of extension arm 20. Ancillary block 82 is mechanically linked to guide block 18 and is movable relative thereto in at least one of six degrees of freedom, such as by means of extension arm 20. A fastener 88 is preferably engageable with each ancillary block 82 and 84 for fixing the ancillary blocks relative to each other or relative to guide block 18.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention is defined only by the claims which follow:

What is claimed is:

1. A drill guide comprising:
   a reference block from which protrudes a location pin adapted to fit in a hole in a mouth of a patient; and
   at least one guide block comprising an extension arm which slides in and out of an aperture formed in said reference block, said extension arm defining a generally straight longitudinal axis extending from said at least one guide block to said reference block, said extension arm being selectively fixable with respect to said reference block at a point on said longitudinal axis by means of a fastener which fastens said extension arm to said reference block. wherein said guide block is formed with a through hole for guiding therethrough a drill bit; and wherein said guide block and said extension arm are rotatable generally about said longitudinal axis.

2. A drill guide according to claim 1 wherein said location pin comprises calibrated markings along an axial length thereof.

3. A drill guide according to claim 1 wherein said extension arm comprises calibrated markings along an axial length thereof.

4. A drill guide according to claim 1 wherein said reference block is rotatable mounted on a base fixed to said location pin such that said reference block may be rotated relative to said location pin generally about a longitudinal axis of said location pin.

5. A drill guide according to claim 1 wherein said location pin is removably attached to said reference block.

6. A drill guide according to claim 1 wherein said extension arm comprises a flexible portion which may be bent relative to said reference block.

7. A drill guide according to claim 1 and wherein said location pin is interchangeable for another said location pin having a different diameter.

8. A drill guide according to claim 1 and wherein said guide block is interchangeable for another said guide block having a different diameter through hole.

9. A drill guide according to claim 1 wherein at least one of said reference block and said guide block comprises a handle.

10. A drill guide according to claim 1 wherein at least one view aperture is formed in said guide block.

11. A drill guide according to claim 1 and comprising at least one ancillary block mechanically linked to said at least one guide block and formed with a through hole for guiding therethrough a drill bit, said ancillary block being movable relative to said at least one guide block in at least one of six degrees of freedom; and a fastener engageable with said ancillary block for fixing said ancillary block relative to said at least one guide block.

12. A drill guide according to claim 1 and comprising a plurality of ancillary blocks each mechanically linked to one another and formed with a through hole for guiding therethrough a drill bit, each said ancillary block being movable relative to another said ancillary block in at least one of six degrees of freedom, wherein one of said ancillary blocks is mechanically linked to said at least one guide block and is movable relative to said at least one guide block in at least one of six degrees of freedom; and a fastener engageable with each said ancillary block for fixing said ancillary block relative to at least one of another said ancillary block and said at least one guide block.

* * * * *